United States Patent
Kim et al.

(10) Patent No.: US 9,658,205 B2
(45) Date of Patent: May 23, 2017

(54) ELECTRODE ARRAY FOR ANALYZING ELECTRICAL CHARACTERISTICS OF CELL SPHEROID

(71) Applicant: Korea Institute of Science and Technology, Seoul (KR)

(72) Inventors: JinSeok Kim, Seoul (KR); Ju Young Jin, Seoul (KR); Jinwoo Jeong, Seoul (KR); Zi Eun Chang, Seoul (KR); Tae Hyung Kim, Seoul (KR); Boo Yong Lee, Seoul (KR); Jin You, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 194 days.

(21) Appl. No.: 14/590,529

(22) Filed: Jan. 6, 2015

(65) Prior Publication Data
US 2015/0192562 A1   Jul. 9, 2015

(30) Foreign Application Priority Data
Jan. 7, 2014   (KR) ........................ 10-2014-0001746

(51) Int. Cl.
*G01N 33/483* (2006.01)
*C12M 1/34* (2006.01)
(Continued)

(52) U.S. Cl.
CPC ........ *G01N 33/4836* (2013.01); *B01L 3/5027* (2013.01); *C12M 23/12* (2013.01); *C12M 41/46* (2013.01)

(58) Field of Classification Search
CPC ... B01F 11/0014; B01L 3/5027; C12M 23/12; C12M 25/08; C12M 33/08; C12M 41/46; G01N 33/48735; G01N 33/5088
(Continued)

(56) References Cited

U.S. PATENT DOCUMENTS

| | | | |
|---|---|---|---|
| 4,894,343 A | * | 1/1990 | Tanaka .................. C12M 23/20 210/498 |
| 8,264,245 B2 | | 9/2012 | Ku et al. |
| 2013/0217064 A1 | | 8/2013 | Robitzki et al. |

FOREIGN PATENT DOCUMENTS

| | | |
|---|---|---|
| JP | 3204875 B2 | 9/2001 |
| JP | 3570715 B2 | 9/2004 |

(Continued)

OTHER PUBLICATIONS

Diemert, S., A. M. Dolga, S. Tobaben, J. Grohm, S. Pfeifer, E. Oexler, and C. Culmsee. "Impedance measurement for real time detection of neuronal cell death." Journal of Neuroscience Methods 203, No. 1 (2012): pp. 69-77.
(Continued)

*Primary Examiner* — Michael Hobbs
(74) *Attorney, Agent, or Firm* — NSIP Law

(57) ABSTRACT

An electrode array for analyzing electrical characteristics of a cell spheroid has a substrate, a groove formed concavely on a top surface of the substrate to receive at least a portion of the cell spheroid, and a plurality of electrodes formed in the substrate, coming into contact with the cell spheroid, and configured to apply or collect electrical signals. Front ends of the plurality of electrodes extend to the groove to form a holding part for holding the cell spheroid, and the cell spheroid is held in the holding part and comes into contact with the plurality of electrodes simultaneously.

11 Claims, 9 Drawing Sheets

(51) Int. Cl.
*B01L 3/00* (2006.01)
*C12M 1/32* (2006.01)

(58) Field of Classification Search
USPC .................................................. 435/287.1
See application file for complete search history.

(56) References Cited

FOREIGN PATENT DOCUMENTS

| | | |
|---|---|---|
| JP | 3801617 B2 | 7/2006 |
| KR | 10-2010-0089927 A | 8/2010 |
| KR | 10-2010-0136181 A | 12/2010 |
| KR | 10-2012-0121910 A | 11/2012 |
| WO | WO 2011/095505 A1 | 8/2011 |

OTHER PUBLICATIONS

Barat, David, Daniel Spencer, Giuseppe Benazzi, Matthew Charles Mowlem, and Hywel Morgan. "Simultaneous high speed optical and impedance analysis of single particles with a microfluidic cytometer." Lab on a Chip 12, No. 1 (2012): pp. 118-126.
Suzuki, Masaaki, Koji Ikeda, Munehiro Yamaguchi, Suguru N. Kudoh, Keiko Yokoyama, Ryota Satoh, Daisuke Ito, Masafumi Nagayama, Tsutomu Uchida, and Kazutoshi Gohara. "Neuronal cell patterning on a multi-electrode array for a network analysis platform." Biomaterials 34, No. 21 (2013): pp. 5210-5217.

* cited by examiner

ELECTRODE ARRAY FOR ANALYZING ELECTRICAL CHARACTERISTICS OF CELL SPHEROID

CROSS-REFERENCE TO RELATED APPLICATION

This application claims priority to Korean Patent Application No. 10-2014-0001746, filed on Jan. 7, 2014, and all the benefits accruing therefrom under 35 U.S.C. §119, the contents of which in its entirety are herein incorporated by reference.

BACKGROUND

1. Field

The present disclosure relates to an electrode array, and more particularly, to an electrode array for analyzing electrical characteristics of a cell spheroid.

2. Description of the Related Art

Cell therapy is known as therapy for functional restoration of cells and tissues that involves cultivating living autogenic, allogeneic, or xenogeneic cells with modification to biological characteristics to obtain a cell therapy product, and injecting the resulting cell therapy product to replace old cells.

In cell therapy, there is a method of transplanting two-dimensionally cultured cells (for example, stem cells), but there are problems; two-dimensional (2D) cell culturing on a large scale is difficult and the probability of survival and an adhesion rate of transplanted cells is very low.

To solve the problems, the use of a so-called "cell spheroid" cultured in three dimensions (3D) as a cell therapy product has been proposed.

A cell spheroid is an assembly of multiple cells, for example, adult stem cells for transplantation, which forms aggregates in 3D.

To make a proper use of a cultured cell spheroid as a cell therapy product, an electrical characteristics analysis needs to be conducted to ascertain a type of cell spheroid, an extent of growth, and a state of synapse connection between cells.

For electrical characteristics analysis of two-dimensionally cultured cells ("2D cells"), a micro electrode array (MEA) system is known.

FIG. 1 is a conceptual diagram of an MEA system 1 according to a related art.

The MEA system 1 places 2D cells in a circular ring-type member 2' formed on a substrate 2 and analyzes the electrical characteristics of the 2D cells.

In the central space of the ring-type member 2', a plurality of pad-type electrodes are arranged in a grid, and the cultured 2D cells come into contact with the plurality of electrodes.

The MEA system 1 includes a stimulation system 4 electrically connected to the electrodes of the substrate 2 to provide electrical stimulation signals to the electrodes, a processing device 5 to analyze signals outputted from the electrodes, and a high speed charge coupled device (CCD) camera 3 to capture images of the cells. Using this construction, the electrical characteristics of the 2D cells may be analyzed.

However, when a 3D cell spheroid is placed on the micro electrode array of the MEA system according to the related art, signal acquisition is locally made only on a region where a contact between the cells and the electrodes is made due to a very small contact area between the electrodes and the cell spheroid.

In the case of the 3D cell spheroid, there is a need to ascertain a state of internal connection between each cell, but the micro electrode array according to the related art is inadequate for that.

SUMMARY

The present disclosure is designed to address the issue of the related art, and therefore, the present disclosure is directed to providing an electrode array optimized for a three-dimensional cell spheroid.

To achieve the object, an electrode array for analyzing electrical characteristics of a cell spheroid according to one aspect of the present disclosure includes a substrate, a groove formed concavely on a top surface of the substrate to receive at least a portion of the cell spheroid, and a plurality of electrodes formed in the substrate, coming into contact with the cell spheroid, and configured to apply or collect electrical signals. Front ends of the plurality of electrodes extend to the groove to form a holding part for holding the cell spheroid, and the cell spheroid is held in the holding part and comes into contact with the plurality of electrodes simultaneously.

According to an exemplary embodiment, the front ends of the plurality of electrodes extend slantly at a predetermined angle toward a bottom surface of the groove.

Also, a sidewall of the groove may be formed slantly such that an area of the bottom surface of the groove is smaller than an area of an opening of the groove, and the front ends of the plurality of electrodes may be formed to extend along the sidewall.

According to another exemplary embodiment, the front ends of the plurality of electrodes are formed to become bent downward by the weight of the cell spheroid when the cell spheroid is held in the holding part in a state that the front ends of the plurality of electrodes extend parallel to an opening of the groove.

Also, the front ends of the plurality of electrodes may be formed to have an elastic property, and when the cell spheroid is removed from the holding part, the front ends of the plurality of electrodes may restore to the state that the front ends extend parallel to the opening of the groove.

Also, the plurality of electrodes may be arranged radially with regard to the groove.

Also, when a first electrode among the plurality of electrodes applies an electrical stimulation to the cell spheroid, a second electrode rather than the first electrode among the plurality of electrodes may be configured to collect an electrical signal outputted from the cell spheroid.

DETAILED DESCRIPTION

Figure 1:
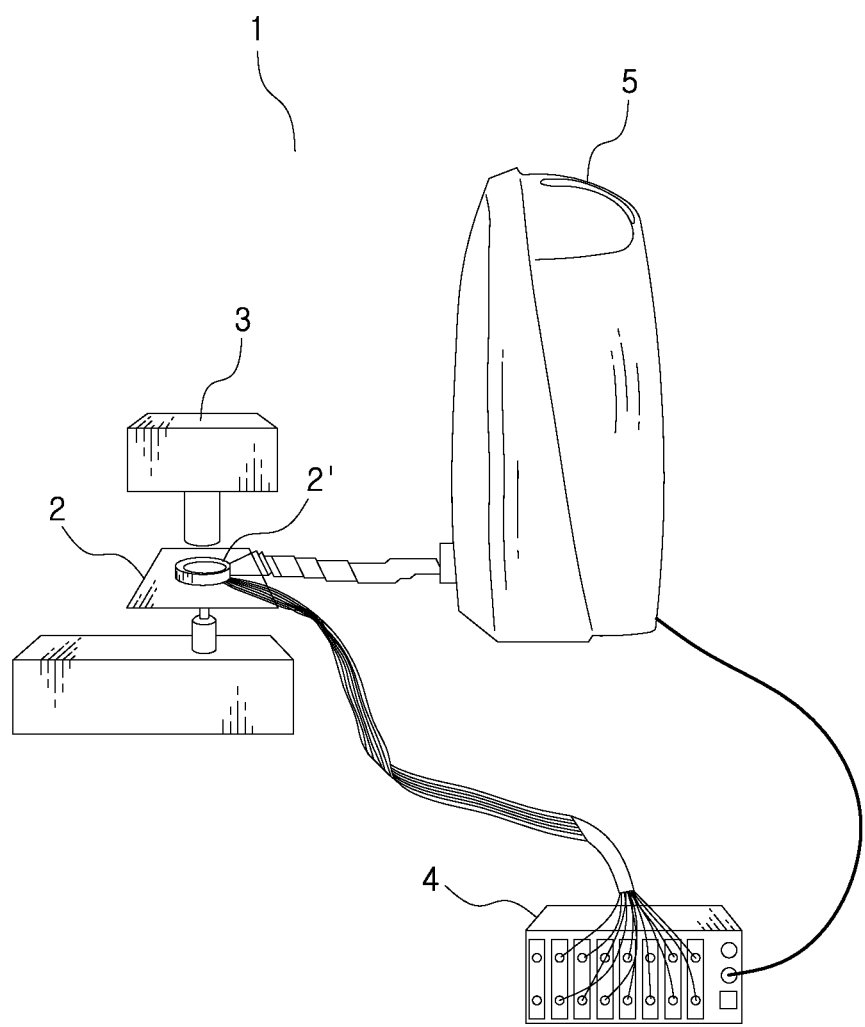
FIG. 1 is a conceptual diagram of a micro electrode array system according to a related art.

Hereinafter, exemplary embodiments of the present disclosure are described with reference to the accompanying drawings. The present disclosure is described with reference to the embodiments illustrated in the drawings, but it is just described as one embodiment, and the technical spirit of the present disclosure and key elements and their operation are not limited thereto.

Figure 2:
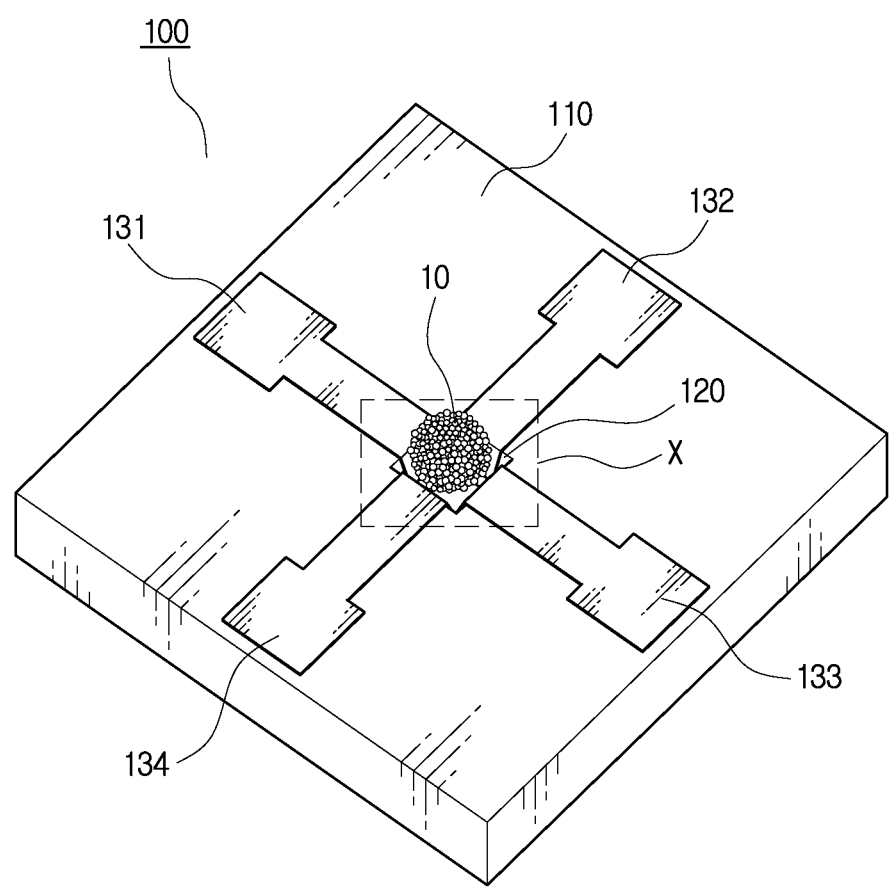
FIG. 2 is a perspective view of an electrode array according to an exemplary embodiment of the present disclosure.
Figure 3:
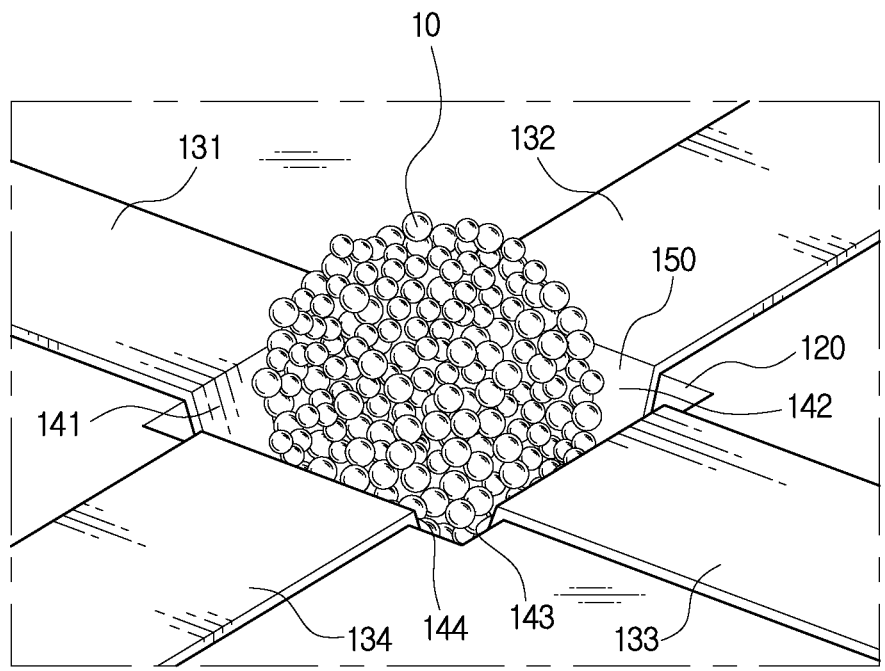
FIG. 3 is an enlarged view of section X of FIG. 2.

FIG. 2 is a perspective view of an electrode array 100 according to an exemplary embodiment of the present disclosure. FIG. 3 is an enlarged view of section X of FIG. 2, and FIG. 4 is a side cross-section view of the electrode array 100 of FIG. 2.

Figure 4:
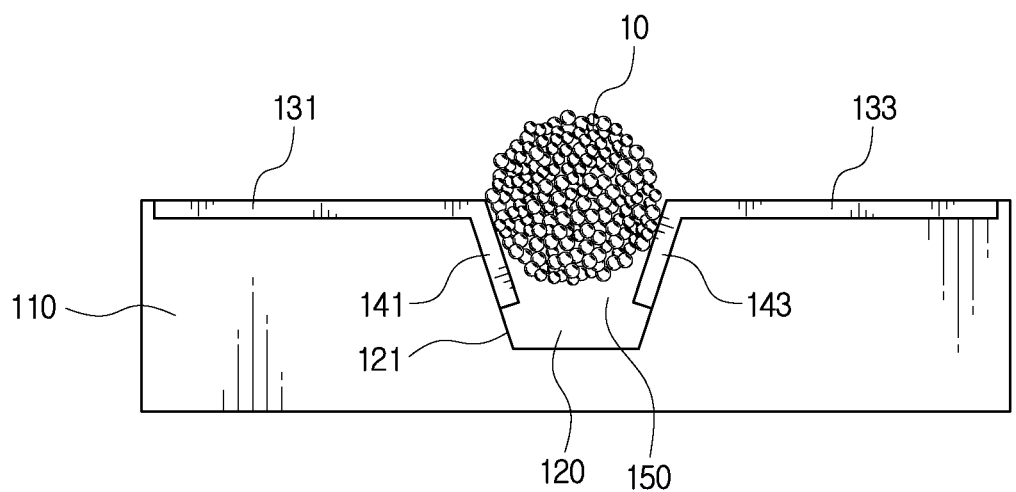
FIG. 4 is a side cross-section view of the electrode array of FIG. 2.

As shown in FIGS. 2 through 4, the electrode array 100 includes a substrate 110 in a shape of a square plate, a groove 120 formed concavely at a center of a top surface of the substrate 110 to receive at least a portion of a cell spheroid 10, and electrodes 131, 132, 133, and 134 extending along the top surface of the substrate 110, coming into contact with the cell spheroid 10, and configured to apply or collect electrical signals. The electrodes 131, 132, 133, and 134 are arranged radially with regard to the groove 120.

As best shown in FIG. 4, the groove 120 is open to the top surface of the substrate 110, and a sidewall 121 is formed slantly such that an area of a bottom surface is smaller than an area of an opening.

Front ends 141, 142, 143, and 144 of the electrodes 131, 132, 133, and 134 extend along the sidewall 121, and extend slantly at a predetermined angle toward the bottom surface of the groove 120.

The front ends 141, 142, 143, and 144 of the electrodes 131, 132, 133, 134 extending to the groove 120 have tips located close to each other with a gap less than a diameter of the cell spheroid 10 to form a holding part 150 for holding the cell spheroid 10.

The cell spheroid 10 is held in the holding part 150 and comes into contact with the plurality of electrodes 131, 132, 133, and 134 simultaneously.

As shown in FIGS. 3 and 4, the cell spheroid 10 is supported by the slanted electrodes 131, 132, 133, and 134 arranged radially, so the cell spheroid 10 is stably held in the electrode array 100 while maximizing a contact area between the electrodes and the cell spheroid 10.

By the electrode array 100 according to this exemplary embodiment, impedance of the cell spheroid 10 may be measured as electrical characteristics of the cell spheroid 10.

Specifically, impedance of the cell spheroid 10 may be measured by measuring impedance (open circuit impedance) of the electrode array 100 in a state that the cell spheroid 10 is not placed on the holding part 50, and measuring impedance (short circuit impedance) of the electrode array 100 in a state that the cell spheroid 10 is placed on the holding part 150.

Figure 5A:
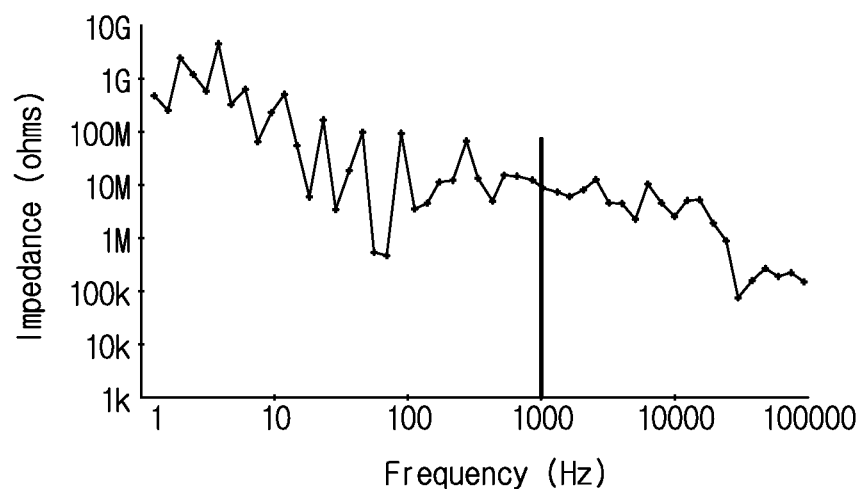
FIGS. 5A and 5B are graphs of impedance measurement results of the electrode array of FIG. 2.
Figure 5B:
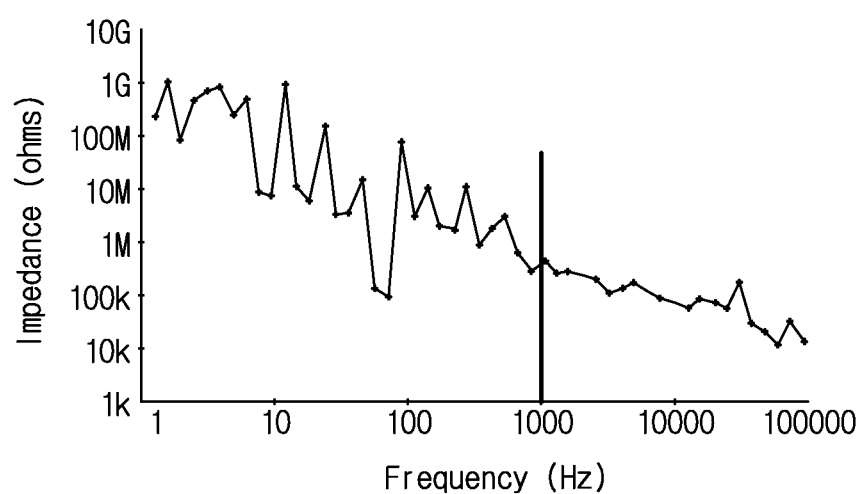

FIGS. 5A and 5B are graphs of impedance measurement results of the electrode array 100 according to this exemplary embodiment. FIG. 5A shows the open circuit impedance, and FIG. 5B shows the short circuit impedance.

The impedance measurement was conducted in the 1 kHz band using a potentiostat, and as the result of measuring through a three-electrode method, it was found that the impedance reduces when the cell spheroid 10 is placed on the holding part 150, leading to a good contact of the electrodes and the cell spheroid 10.

It is known that cell impedance measurement helps in ascertaining a cell type, an extent of growth, and a state of internal electrical connection between cells.

According to this exemplary embodiment, a state of three-dimensional connection between cells forming the cell spheroid 10 may be analyzed more accurately using a spatial arrangement of the plurality of electrodes surrounding the cell spheroid 10 radially.

For example, when the electrode 132 applies an electrical stimulation to the cell spheroid 10 and the other electrodes 133 and 134 collect and analyze electrical signals outputted from the cell spheroid 10, an orientation and a state of connection between the cells in the cell spheroid 10 may be accurately analyzed. In this instance, the electrode 131 is used as a reference electrode.

Figure 6:
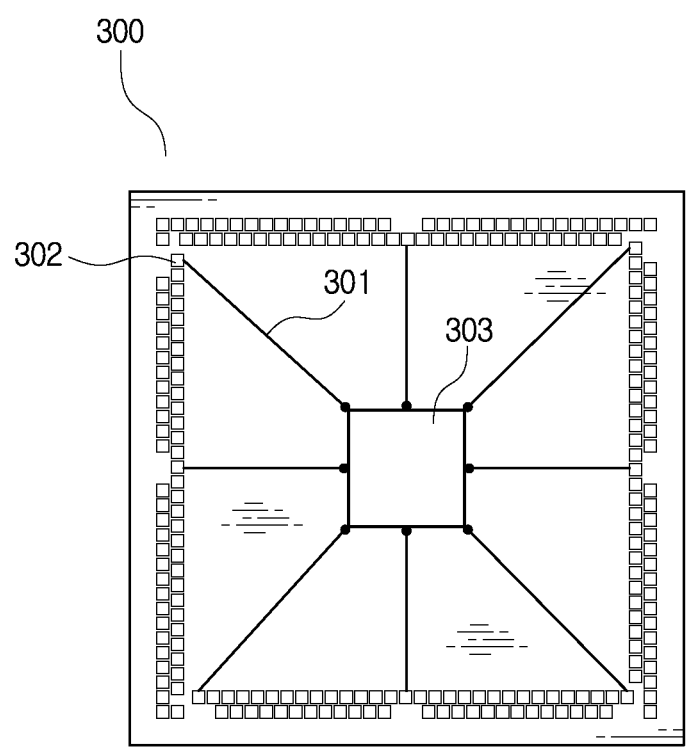
FIG. 6 illustrates a printed circuit board (PCB) substrate to which an electrode array according to an exemplary embodiment may be bonded.

FIG. 6 illustrates a printed circuit board (PCB) substrate 300 to which the electrode array 100 according to this exemplary embodiment may be bonded.

The PCB substrate 300 includes a bonding part 303 at a center to which the electrode array 100 may be bonded, and multiple signal lines 301 and multiple pads 302 to which the electrodes of the electrode array 100 may be electrically connected.

The PCB substrate 300 has the same standard as the substrate 2 of the MEA system 1 according to the related art described in FIG. 1, so the electrode array 100 according to this exemplary embodiment may operate with the MEA system 1 according to the related art. The pads 302 of the PCB substrate 300 may be electrically connected to the stimulation system 4 and the signal processing device 5.

Figure 7:
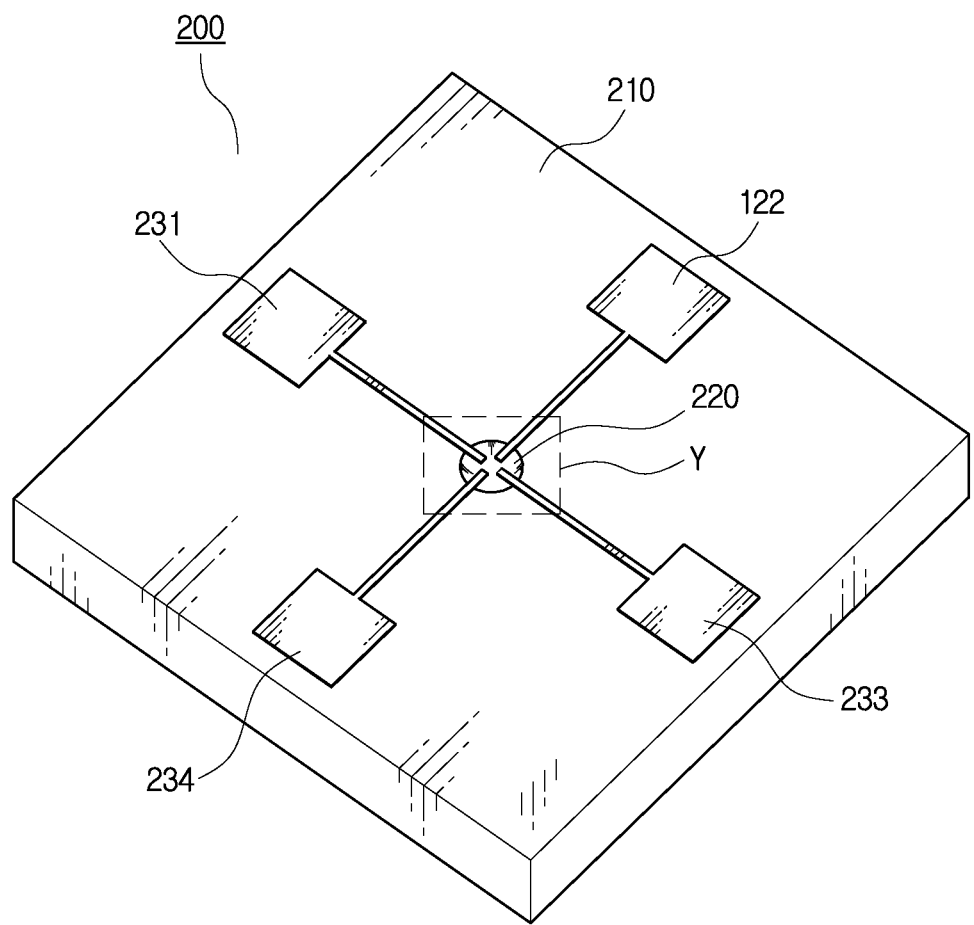
FIG. 7 is a perspective view of an electrode array according to another exemplary embodiment of the present disclosure.
Figure 8A:
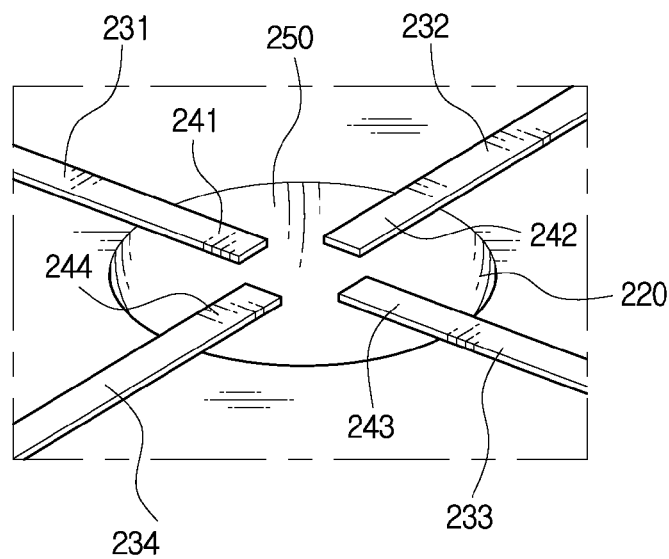
FIGS. 8A and 8B are enlarged views of section Y of FIG. 7.
Figure 8B:
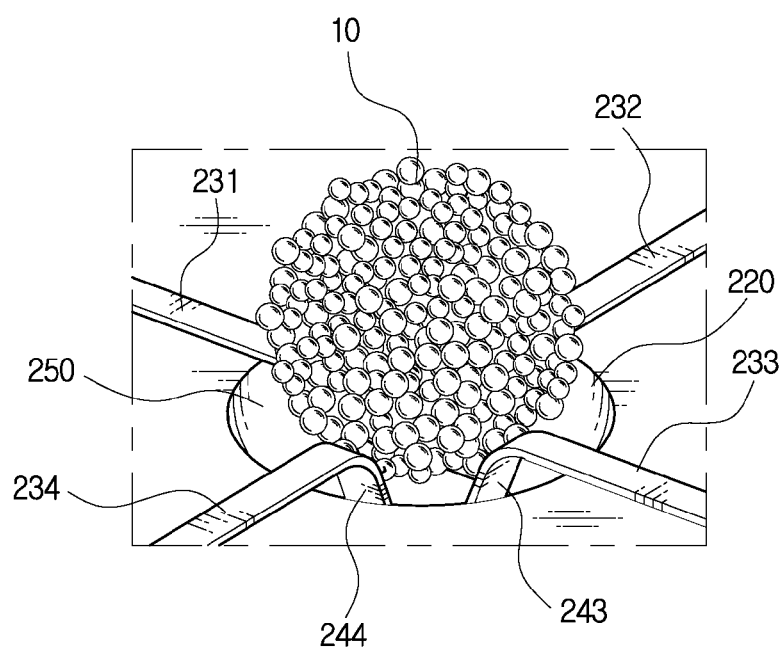

FIG. 7 is a perspective view of an electrode array 200 according to another exemplary embodiment of the present disclosure. FIGS. 8A and 8B are enlarged views of section Y of FIG. 7, and FIGS. 9A and 9B are side cross-sectional view of the electrode array 200 of FIG. 7.

Figure 9A:
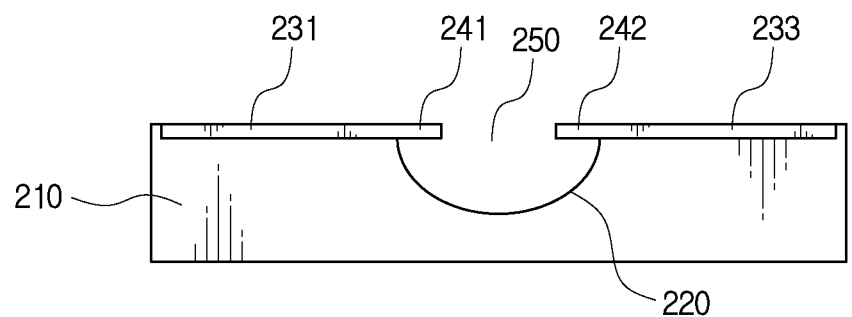
FIGS. 9A and 9B are side cross-sectional view of the electrode array of FIG. 7.
Figure 9B:
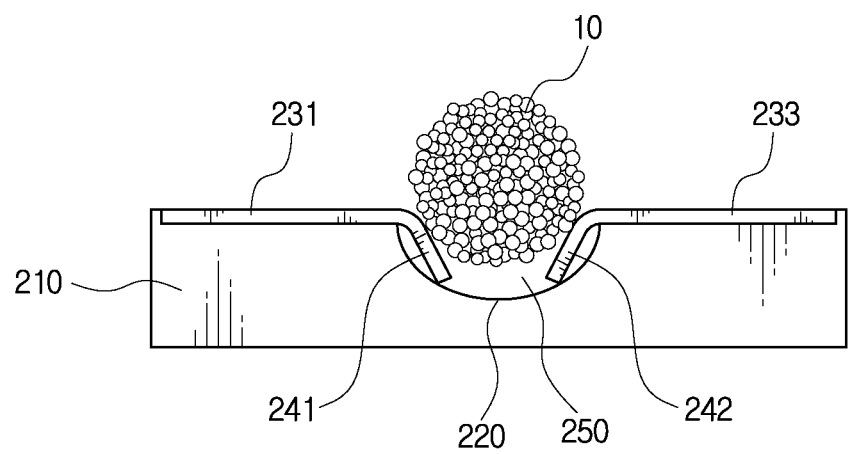

FIGS. 8A and 9A illustrate that the cell spheroid 10 is not held in a holding part 250, and FIGS. 8B and 9B illustrate that the cell spheroid 10 is held in the holding part 250.

As shown in FIGS. 7 through 9, the electrode array 200 includes a substrate 210 in a shape of a square plate, a groove 220 formed concavely at a center of a top surface of the substrate 210 to receive at least a portion of the cell spheroid 10, and a plurality of electrodes 231, 232, 233, and 234 extending along the top surface of the substrate 210, coming into contact with the cell spheroid 10, and configured to apply or collect electrical signals. The electrodes 231, 232, 233, and 234 are arranged radially with regard to the groove 220.

As shown in FIGS. 8A and 9A, when the cell spheroid 10 is not held, front ends 241, 242, 243, and 244 of the electrodes 231, 232, 233, and 234 extend parallel to an opening of the groove 220.

Although not shown in detail, the electrodes 231, 232, 233, and 234 has a double layer structure that an upper part coming into contact with the cell spheroid 10 is made of gold, and a lower part is made of Tiron.

By the lower layer made of Tiron, the front ends 241, 242, 243, and 244 of the electrodes 231, 232, 233, and 234 extending to the groove 220 may have an elastic property.

The front ends 241, 242, 243, and 244 of the electrodes 231, 232, 233, and 234 have tips located close to each other with a gap less than a diameter of the cell spheroid 10 to form the holding part 250 for holding the cell spheroid 10.

The cell spheroid 10 is held in the holding part 250 and comes into contact with the plurality of electrodes 231, 232, 233, and 234 simultaneously.

As shown in FIGS. 8B and 9B, when the cell spheroid 10 is held in the holding part 250, the front ends 241, 242, 243, and 244 of the electrodes 231, 232, 233, and 234 become bent downward by the weight of the cell spheroid 10, and thus a contact area of the electrodes and the cell spheroid 10 is maximized.

When the cell spheroid 10 is removed from the holding part 250, the front ends 241, 242, 243, and 244 of the electrodes 231, 232, 233, and 234 may restore to the state that the front ends 241, 242, 243, and 244 extend parallel to the opening of the groove 220.

The cell spheroid 10 is stably supported by the electrodes 231, 232, 233, and 234 arranged radially and bent slantly downward. Also, as the front ends 241, 242, 243, and 244 of the electrodes 231, 232, 233, and 234 according to this exemplary embodiment become bent in response to the weight of the cell spheroid 10, the holding part 250 corresponding to a diameter of the cell spheroid may be formed. Thus, the cell spheroid of various diameters may be effectively held in the holding part 250.

Similar to the exemplary embodiment previously described, impedance of the cell spheroid 10 may be measured using the electrode array 200.

Figure 10A:
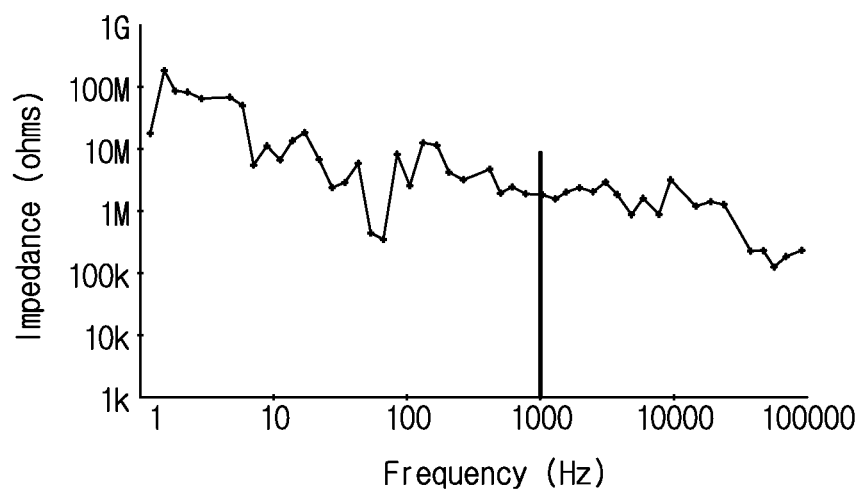
FIGS. 10A and 10B are graphs of impedance measurement results of the electrode array of FIG. 7.
Figure 10B:
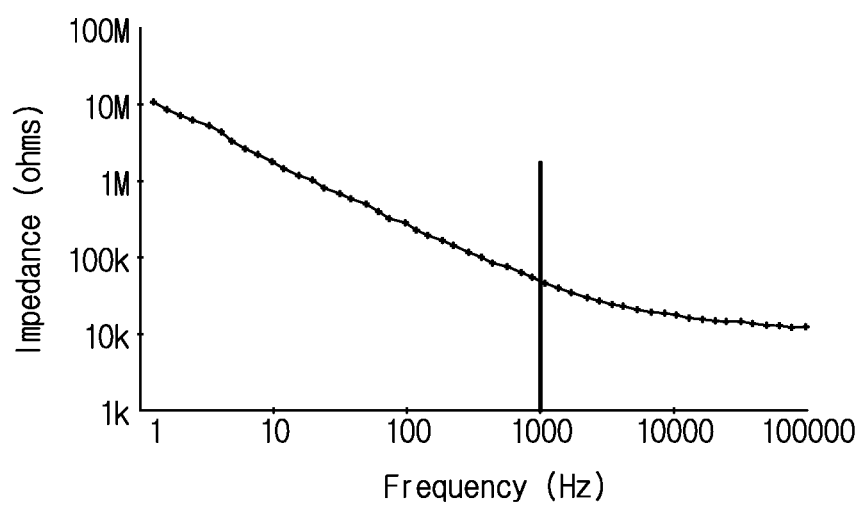

FIGS. 10A and 10B are graphs of impedance measurement results of the electrode array 200 according to this exemplary embodiment. FIG. 10A shows the open circuit impedance, and FIG. 10B shows the short circuit impedance.

The impedance measurement was conducted in the 1 kHz band using a potentiostat, and as the result of measuring through a three-electrode method, it was found that the impedance reduces when the cell spheroid 10 is placed on the holding part 250, leading to a good contact of the electrodes and the cell spheroid 10.

Also, according to this exemplary embodiment, similar to the exemplary embodiment previously described, for example, when the electrode 232 applies an electrical stimulation to the cell spheroid 10 and the other electrodes 233 and 234 collect and analyze electrical signals outputted from the cell spheroid 10, an orientation and a state of connection between the cells in the cell spheroid 10 may be accurately analyzed. In this instance, the electrode 231 is used as a reference electrode.

Also, the electrode array 200 according to this exemplary embodiment may be bonded to the bonding part 303 of the PCB substrate 300 shown in FIG. 6 and be used with the MEA system 1 according to the related art.

The electrode array according to the above exemplary embodiment may maximize a contact area between the cell spheroid 10 and the electrodes and allow for effective collection and analysis of the electrical characteristics of the 3D cells using the structural feature of the electrodes surrounding the cell spheroid 10. Also, the electrode array may be used with the existing MEA system 1 without a need to build a separate system.

What is claimed is:

1. An electrode array for analyzing electrical characteristics of a cell spheroid, the electrode array comprising:
   a substrate;
   a groove formed concavely on a top surface of the substrate to receive at least a portion of the cell spheroid; and
   electrodes formed in the substrate, coming into contact with the cell spheroid, and configured to apply or collect electrical signals,
   wherein front ends of the electrodes extend to the groove to form a holding part for holding the cell spheroid,
   wherein the cell spheroid is held in the holding part and comes into contact with the electrodes simultaneously, and
   wherein the front ends comprise an elastic material that bends into the groove upon placement of the cell spheroid and unbends returning to an original state upon removal of the cell spheroid.

2. The electrode array according to claim 1, wherein the front ends of the electrodes extend slanting at a predetermined angle toward a bottom surface of the groove.

3. The electrode array according to claim 2, wherein a sidewall of the groove is formed slanting such that an area of the bottom surface of the groove is smaller than an area of an opening of the groove, and
   the front ends of the electrodes extend along the sidewall.

4. The electrode array according to claim 1, wherein the front ends of the electrodes are formed to become bent into the groove by the weight of the cell spheroid upon the cell spheroid being held in the holding part in a state that the front ends of the electrodes extend parallel to an opening of the groove.

5. The electrode array according to claim 4, wherein the front ends of the electrodes are formed to have an elastic property, and
   upon the cell spheroid being removed from the holding part, the front ends of the electrodes restore to the state that the front ends extend parallel to the opening of the groove.

6. The electrode array according to claim 1, wherein the electrodes are arranged radially with regard to the groove.

7. The electrode array according to claim 1, wherein upon a first electrode among the electrodes applying an electrical stimulation to the cell spheroid, a second electrode rather than the first electrode among the electrodes is configured to collect an electrical signal outputted from the cell spheroid.

8. The electrode array according to claim 5, wherein the elastic material comprises Tiron.

9. The electrode array according to claim 5, wherein the front ends comprise two layers with the first layer being gold and the second layer being Tiron.

10. The electrode array according to claim 5, wherein the front ends comprise gold and Tiron.

11. An electrode array configured to analyze electrical characteristics of a cell spheroid, the electrode array comprising:
    a substrate;
    a groove formed concavely on a top surface of the substrate to receive at least a portion of the cell spheroid; and
    electrodes formed in the substrate comprising front ends that contact the cell spheroid, the electrodes are configured to apply or collect electrical signals,
    wherein the front ends comprise two layers in which one layer is gold and another layer is Tiron, and
    wherein upon the cell spheroid being placed on the front ends, the front ends bend into the groove, and upon the cell spheroid being removed from contact with the front ends, the front ends unbend and extend parallel to the opening of the groove.

* * * * *